(12) United States Patent
Ferschneider et al.

(10) Patent No.: US 6,224,762 B1
(45) Date of Patent: May 1, 2001

(54) DISTRIBUTOR-MIXER-EXTRACTOR OF FLUIDS AND ASSOCIATED PROCESS

(75) Inventors: Gilles Ferschneider; Jean-Christophe Viguie, both of Saint Symphorien d'Ozon; Olivier Callebert, Rueil Malmaison; Frédéric Hoffmann, Paris, all of (FR)

(73) Assignee: Institut Francais du Petrole, Rueil-Malmaison (FR)

( * ) Notice: Subject to any disclaimer, the term of this patent is extended or adjusted under 35 U.S.C. 154(b) by 0 days.

(21) Appl. No.: 09/389,073

(22) Filed: Sep. 2, 1999

(30) Foreign Application Priority Data

Sep. 2, 1998 (FR) .................................................. 98 10996

(51) Int. Cl.⁷ .................................................. B01D 15/08
(52) U.S. Cl. ....................... 210/198.2; 210/289; 210/656; 96/107
(58) Field of Search .................................. 210/656, 659, 210/198.2, 283, 284, 285, 289, 291, 541; 96/105, 107

(56) References Cited

U.S. PATENT DOCUMENTS

| | | | |
|---|---|---|---|
| 3,214,247 | * 10/1965 | Broughton | 23/288 |
| 3,723,300 | 3/1973 | Carson et al. | 208/146 |
| 4,999,102 | 3/1991 | Cox et al. | 210/137 |
| 5,755,960 | * 5/1998 | Callebert | 210/198.2 |
| 5,846,411 | * 12/1998 | Harter | 210/198.2 |
| 5,972,214 | * 10/1999 | Callebert | 210/198.2 |
| 6,015,491 | * 1/2000 | Renard | 210/198.2 |
| 6,024,871 | * 2/2000 | Harter | 210/198.2 |
| 6,156,197 | * 12/2000 | Dessapt | 210/198.2 |

FOREIGN PATENT DOCUMENTS

| | | | |
|---|---|---|---|
| 0 769 316 | 4/1997 | (EP) | 210/198.2 |
| 95/03867 | 2/1995 | (WO) | 210/198.2 |

* cited by examiner

Primary Examiner—Ernest G. Therkorn
(74) Attorney, Agent, or Firm—Millen White Zelano & Branigan (57) ABSTRACT

Device (DME) or panel for collecting, distributing, mixing or drawing off several fluids, at least one main fluid and at least two secondary fluids, that comprises at least:

means for collecting a main fluid (3, 9), at least two injection and/or draw-off rails (6, 7) that allow the passage of secondary fluids, at least two mixing chambers (11a, 11b) that communicate with injection and/or draw-off rails (6, 7) with orifices or passages (6i, 7i), means (12, 4) for redistributing the fluid that is obtained from said mixing chambers, means (5a, 5b) for separating collecting and redistributing means and draw-off rails (6, 7) are arranged one above the other, and mixing chambers (11a, 11b) are arranged on both sides of the rails and symmetrically relative to the orifices that have an injection function.

22 Claims, 5 Drawing Sheets

DISTRIBUTOR-MIXER-EXTRACTOR OF FLUIDS AND ASSOCIATED PROCESS

CROSS REFERENCE TO RELATED APPLICATION

This application is related to Ser. No. 09/389,071, filed Sep. 2, 1999, now U.S. Pat. No. 6,156,197.

This invention relates to a device, or, in abbreviated form, DME, and a process that makes it possible to collect, distribute, mix, add and/or draw off several fluids (at least one main fluid and at least two secondary fluids).

The invention can be applied in particular in the area of chromatography for fluids in a gaseous state, liquid state or supercritical state.

The invention relates to a DME that can be used in a separation process in a simulated moving bed of paraxylene that is contained in a mixture of xylenes and ethylbenzene, for the purpose of terephthalic acid synthesis, an intermediate petrochemical product in the production of textiles.

The invention can also be used for separating, for example, a xylene and ethylbenzene isomer mixture, a mixture of a compound that is selected from saturated fatty acids and their esters, a mixture of paraffin and olefins, a mixture of isoparaffins and normal paraffins, and other compounds.

The device according to the invention can operate in a liquid phase, a vapor phase or in a supercritical phase and in all of the separation areas, in particular in chemistry, petrochemistry or petroleum.

In the area of separation processes, it is customary to rely on simulated moving bed systems to separate the elements that comprise, for example, at least two different chemical compounds or else two isomers of the same compound. The adsorption material that is used is, for example, a solid.

The technological background that illustrates the implementation of an adsorption device with simulated countercurrent is described in, for example, U.S. Pat. No. 2,985,589.

In these processes, a main fluid that is introduced via a pump flows through the solid bed along the central axis of the column. To obtain the best performances of this process, it is important that the main fluid flows through the adsorbent according to a piston-type flow (plug flow), i.e., to have a composition and a flow front that are as uniform as possible at all points of the surface of the adsorbent bed.

The prior art describes various means that attempt to obtain and to maintain such a flow.

For applications with simulated countercurrent, the device that is described in U.S. Pat. No. 3,214,247 shows a structure that comprises an upper grid, a lower grid for holding particles and two non-perforated horizontal baffles that are positioned between these two grids. The fluids are added or extracted from a central space between the baffles or deflectors by a hose that traverses the entire section of the device. Such a device makes it possible to remix the main fluid while flowing in the column and also to ensure a good mixing of a fluid that is added to the main fluid.

It is also possible to mention the two U.S. Pat. No. 5,792,346 and U.S. Pat No. 5,755,960 that disclose fluid distribution panels or DME whose function in particular is to mix, extract or add fluids. These DME are connected to fluid distributing-collecting circuits whose function in particular is to homogenize the passage time of the particles of the fluid from outside of the column to the panels and conversely from a panel to an outside collecting network, for example.

Actually, the dispersion into the composition of the flow and in the passage time of the fluid particles can also be obtained in the way in which the fluids are distributed or extracted up to the DME or from the DME.

Some distributing or collecting circuits are suitable for reducing the dispersion time of the fluids. The geometry of these circuits is generally adapted to the geometry of the plates and to the arrangement of the DME at these plates.

For example, in the U.S. Pat. No. 5,792,346, the circuit for distributing or extracting secondary fluids shows a distribution symmetry and an isolength of the transfer lines of the fluids. These circuits allow a distribution of the separator-type fluids or a radial distribution from or to the center of the separation column.

In U.S. Pat. No. 5,755,960, the distributing-collecting circuit consists of several radial hoses that comprise several branches for distributing or collecting secondary fluids to or from each panel that forms a distribution plate. The branches are distributed over the whole or over a portion of the length of the radial-feed hose to which they are connected. Another variant consists in distributing the fluids from a ring or half-rings that are positioned on the periphery of the column. The fluid transfer hoses up to a DME are distributed over the entire length of the ring or half-rings.

The object of this invention is to provide a device that is referred to by the term DME whose function in particular is to collect, mix, extract or remix fluids, that has a specific arrangement of two mixing chambers and a distributing-collecting rail to ensure the most symmetrical distribution or collection of fluids possible.

Its object in particular is to improve the mixing of fluids and thereby the resulting composition. It makes it possible to obtain a plug flow and a flow composition through the adsorbent that is the most homogeneous possible.

Throughout the rest of the description, a level 1 chamber is defined as a chamber whose function is to divide a fluid at least in two or to collect two fluid flows, and a level 2 chamber is defined as a chamber that ensures the division at least in two of a fluid that is obtained from a level 1 chamber or the collection of two fluid flows to send them to a level 1 chamber.

The term DME refers to a panel whose function in particular is to collect, mix, extract or remix one or more fluids.

This invention relates to a device (DME in abbreviated form) or panel for collecting, distributing, mixing or drawing off several fluids, at least one main fluid and at least two secondary fluids, that comprises at least:

means for collecting a main fluid, at least two injection and/or draw-off rails that allow the passage of secondary fluids, at least two mixing chambers that communicate with injection and/or draw-off rails with orifices or passages, means for redistributing the fluid that is obtained from said mixing chambers, means (5a, 5b) for separating collecting and redistributing means.

It is characterized in that the rails are arranged one above the other and in that said mixing chambers are arranged on both sides of at least one of said rails.

The mixing chambers are arranged, for example, relative to the orifices to obtain an injection or a draw-off of the fluid or fluids that is the most uniform possible in the mixing chamber or chambers.

The injection rails and the mixing chambers are located, for example, approximately in the center of gravity of the surface of said DME.

The upper rail can be provided with at least two hoses, and the lower rail can be provided with at least one hose, whereby the hoses are arranged to ensure the circulation of secondary fluids most symmetrically in the rails and the mixing chambers.

The passage openings of a secondary fluid of the rail or rails whose function is to inject secondary fluids into a mixing chamber have an axis such that the fluid that is obtained strikes at least a portion of a solid wall of one of the elements of the DME.

The lower circuit or lower rail of the secondary fluid has its lower wall arranged, for example, at the lower grid (to improve the mechanical behavior of the unit).

This invention also relates to a device or a column for separation that comprises, for example, a chamber, whereby the chamber comprises at least a first adsorbent bed ($A_1$) and at least a second adsorbent bed ($A_2$), whereby the beds are separated by a plate Pi that comprises one or more panels (DME) that have one of the characteristics of Claims 1 to 5, whereby the DME are connected with the outside via connecting hoses.

The upper rail of a DME may have a function of collecting fluids, and the lower rail of a DME may have a function of injecting fluids.

The upper rail of a DME has, for example, a function of injecting fluids, and the lower rail of a DME has a function of collecting fluids.

The upper and lower rails of a DME may each have a fluid injecting-collecting function.

The openings of the rail or rails that have an injection function are arranged, for example, such that the fluid jet that passes through the orifice strikes at least one portion of a solid wall of one of the elements of the DME.

The openings of the rails can be arranged alternately or at random.

The parameters of the rails and the openings are selected, for example, from among the following data:
- a diameter of the openings of, for example, between 2 and 15 mm and preferably between 4 and 7 mm, whereby the openings may have an injection function,
- a perforation span of between 25 and 400 mm and preferably between 50 and 200 mm,
- a rate of flow of the fluids of between 3–20 m/s and preferably between 5–15 m/s; the value of the span that is under consideration with the value of the rate makes it possible to obtain a good mixing of the secondary fluid and the main fluid.

The parameters of the mixing chambers and the openings of the chambers are selected, for example, from among the following values:
- a diameter of openings of between 5 and 50 mm, and preferably between 10 and 25 mm,
- a perforation span that is selected from the interval 25–400 mm and preferably in the interval of 50–200 mm,
- a rate of flow of the mixture of between 0.5 and 3.5 m/s and preferably between 1.0–2.0 m/s.

The device may comprise at least two fluid distribution systems that have the following characteristics:
- said distribution system is placed on the periphery of said chamber,
- said distribution system is connected with at least one distribution plate (Pi), and said distribution system comprises:
  - at least one hose that makes it possible for the device and the outside to communicate,
  - at least one so-called level 1 chamber ($N_1$) that ensures a two-way division or collection of the fluid flow, whereby said chamber is connected with the communication hose,
  - at least two so-called level 2 chambers ($N_{20}$, $N_{21}$), whereby the level 2 chambers ensure a two-way division or collection of the flow of the fluid that comes from or is sent to level 1 chamber ($N_1$),
  - one or more connecting hoses ($C(N_{20})_j$, $C(N_{21})j$)) that extend between a level 2 chamber ($N_{20}$, $N_{21}$) and at least one of panels (DME) of a plate (Pi), whereby points rj for connecting connecting hoses are located in a zone ($Z_{20}$, $Z_{21}$), whereby the positioning of this zone is determined by an angle a counting from one of the radial axes of said plate (Pi), whereby each of the fluid connecting hoses has a length li, whereby the value of each of lengths li, of angle $\alpha$ and of length Zr of the zone are selected so that the passage time of the fluids between a panel (DME) of a plate (Pi) and the hose for introducing or extracting the fluids is essentially identical for all of the fluids.

The minimum dispersion time that is obtained is equal to, for example, the difference in time between the first and the last hole of supplied DME, which is at most 10 s and preferably less than 5 s.

Plate Pi can be divided into four sectors.

Each plate is divided into, for example, several panels or DME according to a cutaway in parallels (of meridian type).

Angle $\alpha$ is, for example, between 30 and 90 degrees, preferably between 50 and 60 degrees, and length Zr that corresponds to the angle sector is between 3 and 30 degrees and preferably between 7 and 15 degrees.

This invention also relates to a process that makes it possible to separate at least one compound from a mixture or an element by adsorption. It is characterized in that a main fluid, from which it is sought to separate some compounds, is brought into contact with an adsorbent that is selected as a function of its ability to separate the compounds, and the secondary fluids are injected and/or extracted via a panel or DME to collect, distribute, mix or draw-off several fluids, at least one main fluid and at least two secondary fluids, that comprises at least:
- means for collecting a main fluid,
- at least two injection and/or draw-off rails that allow the passage of secondary fluids,
- at least two mixing chambers that communicate with injection or draw-off rails with orifices or passages,
- means for redistributing the fluid that is obtained from said mixing chambers,
- means for separating collecting and redistributing spaces, whereby the rails are arranged one above the other, and the mixing chambers are arranged on both sides of the rails.

It is possible to inject a fluid in the most uniform manner possible into the mixing chambers by passing through the orifices whose function is injection.

It is possible to group the fluids by function (injection/or draw-off) or by nature or by flow rate value.

The device and the process according to the invention are well suited for separating a feedstock by chromatography for fluids in a gaseous state, liquid state or supercritical state.

The device and the process according to the invention are also well suited for the separation of paraxylene in a simulated moving bed.

Relative to the devices of the prior art, the DME according to the invention and the separation device that comprises one or more of these DME have in particular the following advantages:

because of the good distribution symmetry of the secondary fluids and the main fluid, the mixing is improved over the entire plate, which imparts a more homogenous composition and a general plug flow to the circulating flow in the separation device, the distribution or the extraction of fluids in or from a DME is carried out with a distributing-collecting system that ensures a minimum dispersion between the passage times of the fluid flows for the same plate, an approximately uniform flow density over the entire column, a homogeneous spatial distribution of the flows of secondary fluids over the surface of the plate.

BRIEF DESCRIPTION OF THE DRAWINGS

Other characteristics and advantages of the device according to the invention will emerge from reading the description of examples that are given below as an illustrative and nonlimiting example by referring to the accompanying drawings, where.

DESCRIPTION OF THE PREFERRED EMBODIMENTS

The example that is given below relates to, in an illustrative and nonlimiting way, an application of DME according to the invention that is arranged between two granular solid beds or adsorbent beds in a separation column. The separation column is, for example, intended to separate the paraxylene. The fluids that are referred to as "secondary fluids" can be the feedstock, the extract or the raffinate that are obtained by separation or else the desorbent that is used to extract from adsorbent beds the components that have been adsorbed during the separation process.

Figure 1:
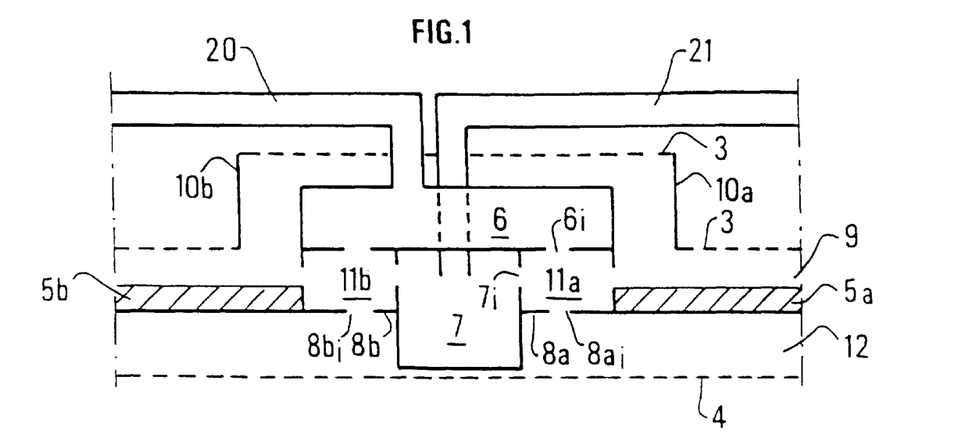
FIG. 1 represents in a detailed manner an embodiment of a panel of DME according to the invention, and FIGS. 1A, 1B and 1C correspond to cutaway views and top views of several variant embodiments.

An elementary panel or DME whose function in particular is to collect, mix, extract or remix the fluids is divided with a distributing-collecting rail into two approximately equal surfaces. The distributing-collecting rail is formed by, for example, the superposition of two rectangular-section boxes or rails.

A panel or DME comprises an upper grid 3 and a lower grid 4 by taking into consideration the direction of circulation of the main fluid inside the separation column. Upper grid 3 ensures at least in part the collection of the main fluid, whereas lower grid 4 ensures at least in part the redistribution of the mixture that is obtained from the mixing chamber over the entire panel and over the entire surface of an adsorbent bed that is arranged below.

Between these two grids, for example of slot type, are arranged various elements:

two deflectors 5a, 5b, or baffles whose function in particular is to separate the collecting channel and the distributing channel that are described below, two rails 6, 7 that allow the passage of secondary fluids; these rails are arranged one above the other, for example. Upper rail 6 can be located above the deflectors, whereas lower circuit 7 can be positioned between two deflectors 5a, 5b and extend according to its height below the deflectors.

These circuits or rails 6 and 7 are provided on at least one of their walls with one or more orifices that are referenced respectively 6i and 7i. In FIG. 1, orifices 6i are arranged on the lower wall of rail 6, and orifices 7i are arranged on the lateral walls of rail 7. The axes of orifices 7i are arranged so that the flows of fluids strike the end of deflectors 5a, 5b, for example.

Each rail is perforated symmetrically and respectively on its lower face or its lateral face for upper rail 6 and on these lateral faces for lower rail 7. Specifications on distribution and the size of the orifices are explained below:

in the extension of deflectors 5a and 5b are arranged perforated plates, respectively 8a, 8b (openings or slots 8ai, 8bi). These plates 8a, 8b extend up to the lateral walls of rail 7, for example. Orifices 8ai, 8bi are, for example, calibrated to promote the mixing of fluids before its passage to distribution space 12, a space 9 for collecting the main fluid that is delimited by upper grid 3, the top of rail 6, a lateral wall of rail 6, deflectors 5a and 5b (for reasons of mechanical design, the variant that is shown in the figure shows a three-part grid, whereby the parts are connected to one another via walls 10a, 10b). This space 9 makes it possible to drain the main fluid to the mixing chambers, two mixing chambers 11a, 11b are arranged on both sides of distributing-collecting rail 7.

Preferably, the chambers are arranged, for example, relative to orifices 6i, 7i of rail 6 or 7 or both, whose function will be to inject one or more fluids into the mixing chambers. They will be arranged to ensure the most homogenous, uniform or symmetrical fluid injection that is possible in the entire mixing chamber, for example.

Mixing chamber 11a is delimited by, for example, a portion of the wall of rail 6, a lateral wall of rail 7, deflector 5a and perforated plate 8a. Mixing chamber 11b is delimited in the same way by a lateral wall of rail 7, a portion of the lower wall of rail 6, deflector 5b and perforated plate 8b.

The chambers are preferably positioned in the center of gravity of the surface of the DME.

The main fluid that is collected by grid 3 travels from collecting space 9 to mixing chambers 11a, 11b in the form of a fluid space via the slot that is formed between the upper rail and the upper wall of one of the deflectors:

A space 12 for redistributing the mixture that is obtained from mixing chambers 11a, 11b. This space is delimited by lower grid 4, the lower wall of lower rail 7, when the latter is not arranged at the same level as grid 4 and mixing chambers 11a, 11b as well as two deflectors 5a, 5b.

Because of the arrangement of the orifices, mixing chambers and distributing and/or collecting rails, the mixture that is obtained in the redistribution space has a composition whose homogeneity is improved relative to the devices of the prior art.

Rails or circuits 6, 7 that are intended for passage of secondary fluids, as well as the two mixing chambers, have, for example, elongated rectangular shapes.

According to a variant embodiment, it is possible to arrange between the lower end of wall 1a, 10b and corresponding deflector 5a, 5b, means that make it possible to create a series of calibrated orifices or slots to inject the main fluid in the form of several jets into the mixing chambers.

The mixing chambers may comprise a series of calibrated orifices 8ai, 8bi whose purpose is to promote the mixture before its passage to distribution space 12 or the function of the chamber.

The distribution of various orifices at rails 6, 7 and the mixing chamber is selected so that in the injection function, the fluids that are injected into the mixing chamber will strike at least a portion of the solid wall of one of the elements of the DME, which promotes the mixing of the fluids.

For example, when rail 6 has a draw-off function and rail 7 has an injection function, the geometric and dimensional data for orifices $6i$, $7i$ relative to the distribution rails as well as their distribution on the various walls will be selected from among, for example, the following values:

- a perforation span of between 25 and 400 mm and preferably between 50 and 200 mm,
- a diameter of between 2 and 15 mm and preferably in the range of 4 to 7 mm,
- a rate of flow of the fluids of between 3–20 m/s and preferably between 5–15 m/s, whereby the rate makes it possible to feed all of the orifices for each of circuits 6, 7 in the most homogenous way possible. The value of the span that is being considered with the value of the rate makes it possible to obtain a good mixing of the secondary fluid and the main fluid.

The criteria that are given for the selection of values of the rate of flow and the perforation span are valid regardless of the shape of the orifices.

The configuration and the criteria for sizing of the draw-off network are approximately identical to those of the injection network. A difference may exist in the perforation plane of the draw-off rail. According to a variant embodiment, the span between the openings of the draw-off rail are approximately equal to twice that of the injection rail. Orifices $6i$, $7i$ will be arranged, for example, alternately or at random.

Outlet openings $8ai$, $8bi$ of the mixing chamber or orifices for passage of the mixture will have the following characteristics:

- a perforation span that is selected from the interval 25–40 mm and preferably in the interval 50–200 mm,
- a diameter of between 5 and 50 mm, and preferably between 10 and 25 mm,
- a rate of flow of the mixture of between 0.5 and 3.5 m/s and preferably between 1.0–2.0 m/s.

The orifices or passage of the fluids can have any type of geometry, such as a single slot, several slots or else holes.

The space for collecting the main fluid preferably has a shape that is suited for minimizing dead volumes and turbulence of the fluids. It has a height of between, for example, 3 and 25 mm and preferably between 7 and 15 mm, and an approximately rectangular or conical shape. It may have the characteristics that are mentioned in above-mentioned U.S. Pat. No. 5,7555,960 of the applicant.

The space for redistributing the mixture in front of the grid will be determined, for example, by taking into consideration the physical characteristics of the main fluid.

The volume of the mixing chamber will preferably be suitable for minimizing the dead volumes. Its dimensions will be selected from among those that are given in one of above-mentioned U.S. Pat. No. 5,792,346 or U.S. Pat. No. 5,755.,960.

Any turbulence-promoting means can be added to the inside of the mixing chamber. These means can be presented in the form of obstacles, baffles or any other means that are intended to increase the effectiveness of the mixture. The volume of this chamber will be selected in a small enough size to minimize the influence of retromixing phenomena.

Figure 1A:
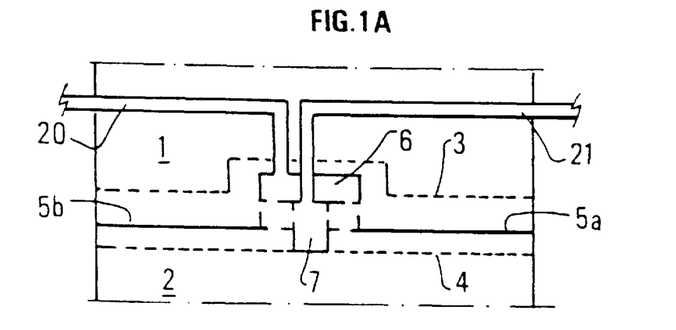

FIG. 1A shows a diagram of a section that shows an arrangement example of a DME between two adsorbent beds 1 and 2 of a separation column. Each of the rails of the DME communicates with the outside via hoses 20, 21.

Figures 1B, 1C:
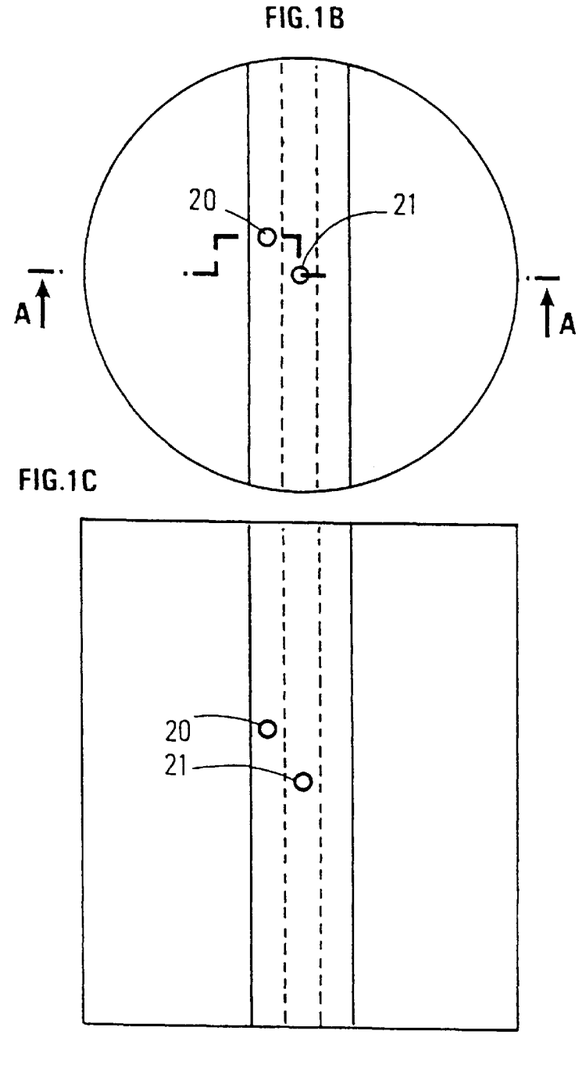

FIG. 1B shows a top view of a circular plate of a separation column that comprises a panel or DME according to the invention.

FIG. 1C shows another variant where the plate has a rectangular shape.

Figure 2A:
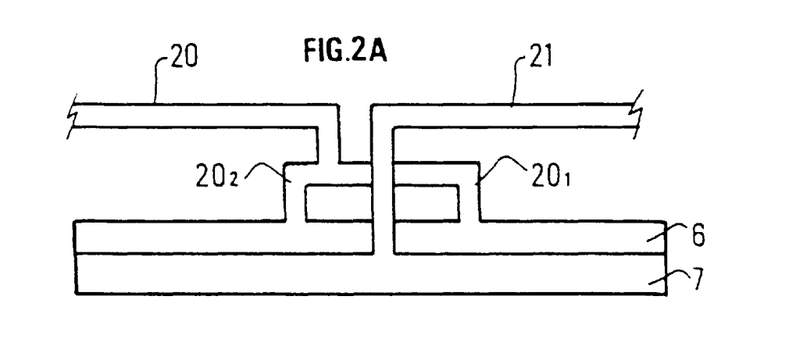
FIGS. 2A and 2B represent a top view and a section of a panel feed example.
Figure 2B:
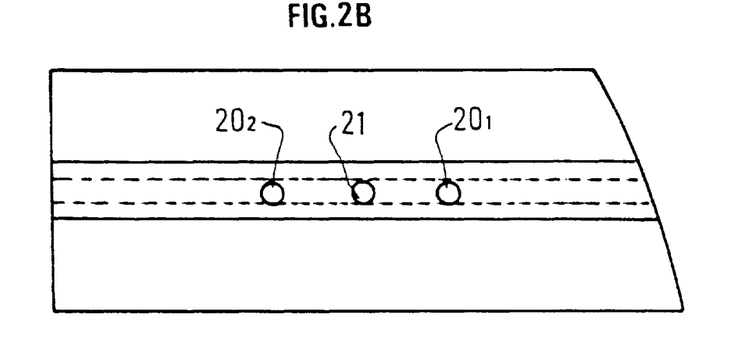

FIGS. 2A and 2B show diagrams of a top view and a section of a hose arrangement example that makes it possible to link a panel with the outside of the separation column.

This example is given as an illustrative and nonlimiting example in the case where the rails are arranged one above the other, whereby the central axis for each of the rails is essentially aligned, and the function of the upper rail is to extract fluid whereas the function of the lower rail is to inject a fluid into the mixing chamber.

Upper circuit 6 that is used, for example, to extract a secondary fluid, comprises at least two extraction hoses $20_1$ and $20_2$ that are connected to a main hose 20. A hose 21 makes it possible to inject a fluid that is obtained from the outside of the column in lower distribution rail 7.

Two hoses $20_1$ and $20_2$ are arranged on both sides of hose 21 such that the fluid is injected in the most symmetrical and homogenous manner possible into the upper rail. Hose 21 is preferably arranged in the vicinity of the axis of rail 6.

Rails 6 and 7 can ensure various functions, distribution or extraction or else both according to the grouping of the secondary fluids outside of the separation column of which some examples are given below.

According to a variant embodiment, a DME or panel can also be divided into several injecting-collecting systems and therefore comprise several superposed rail systems. In this case, hoses 20, 21 are divided to be arranged relative to the upper and lower rails in an essentially identical manner to the one that is described in FIGS. 2A and 2B.

Figure 3:
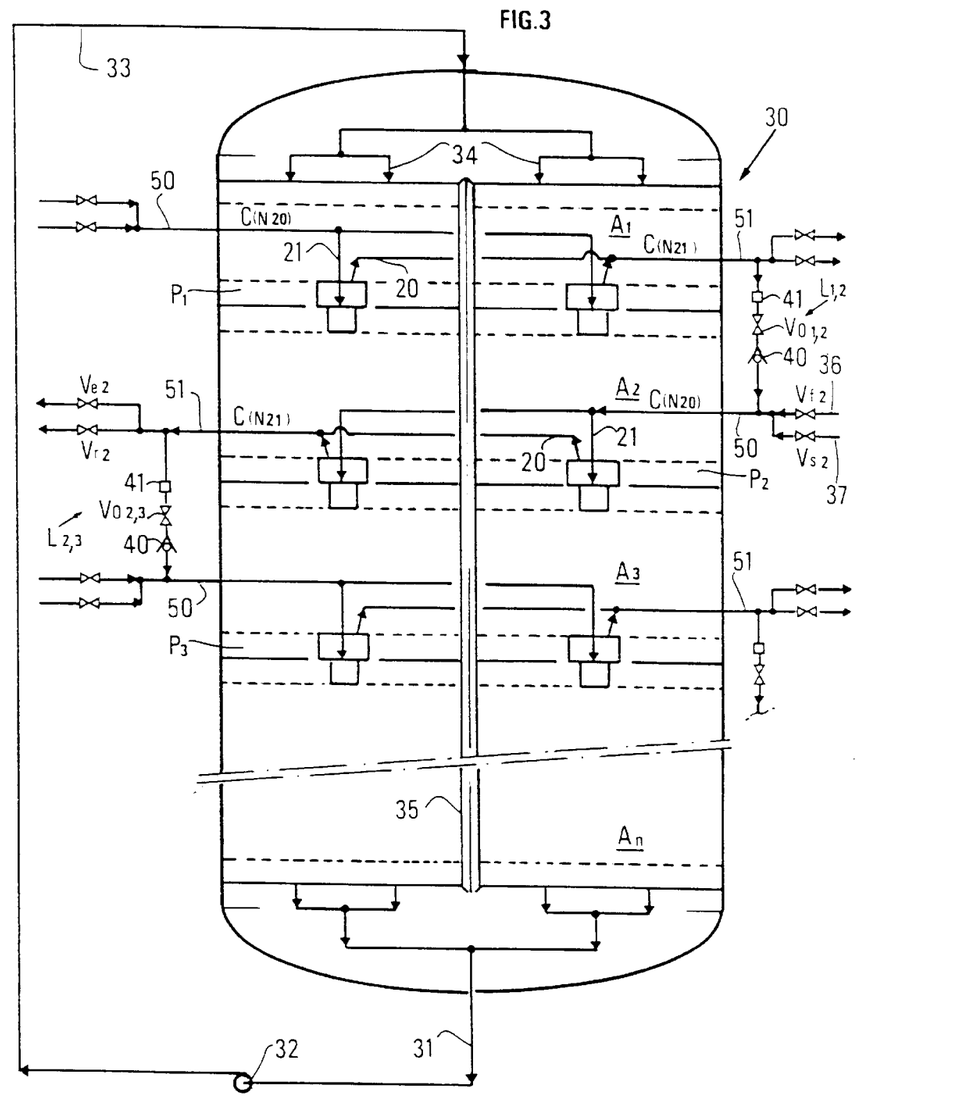
FIG. 3 shows a diagram of a longitudinal section of a separation column that comprises several plates that comprise panels according to the invention.

To better understand the advantages that are provided by the DME, FIG. 3 shows a column for separation by chromatography in a simulated moving bed that comprises distribution panels as described in FIGS. 1, 2A and 2B.

The column comprises a chamber 30 that is, for example, essentially cylindrical and is filled with an adsorbent that is distributed in, for example, several adsorbent beds $A_1$ to $A_n$, a fluid distributor plate Pi that is arranged between each adsorbent bed, and a plate that comprises one or more panels or DME.

The main fluid is drawn off from the lower end of the column via a line 31 to be recycled via a pump 32 and a line 33 at the upper end of this column where it is introduced into upper adsorbent bed $A_1$ via lines 34. The column can also comprise a central beam 35 that is aligned essentially along the vertical axis of the chamber, for example for columns of large diameter.

In this embodiment, the column also comprises a by-pass line Li,j between the plates, whose operating principle is provided in Patent Application FR 97/16,273, whose teaching is incorporated by reference. Such a process makes it possible in particular to increase the purity of the products that are obtained by such a process.

For the separation of paraxylene from a xylene feedstock, two columns of twelve beds each are used, whereby the twenty-four beds are divided into at least four zones, whereby each zone is delimited by an injection of a fluid from the outside of the column (of the desorbent or the feedstock, for example) and a draw-off of another fluid (extract or raffinate, for example). For example, five beds are reserved for zone 1, nine beds for zone II, seven beds for zone III and finally three beds for zone IV.

The panels of a plate Pi are linked with, for example, the outside of the column via secondary fluid transfer lines (feedstock injection line 36, desorbent injection line, draw-off line 38 of an extract and draw-off line of a raffinate 39, and optionally an injection line of a fifth back flush fluid). The back flush lines are not shown in the figure for reasons of simplification.

Each of these lines is equipped with a sequential valve that is shown symbolically by Vfi, Vei, Vsi and Vri, where index i corresponds to plate Pi and where f refers to the feedstock, e the extract, s the desorbent and r the raffinate. The set of these valves is connected to means for sequential swapping-out that are suited for periodically advancing each injection point of secondary fluid or draw-off of secondary fluid from a bed in the direction of circulation of the main fluid, i.e., from top to bottom to obtain an operation in a simulated moving bed.

The circuit that makes it possible to carry out the by-pass and to obtain a composition of a fluid that is essentially identical at all points of a plate comprises a bypass line Li,j that connects two introduction or draw-off hoses, and two plates. According to the prior art, a bypass line comprises at least one of the devices that are mentioned below, by itself or in combination, namely a nonreturn valve 40, a flowmeter 41, a control valve VOi,j that may or may not be slaved to the flowmeter. A pump that is optionally arranged on the bypass line optionally does not ensure an adequate pressure drop.

The valve that equips the bypass or bypass line is referenced VOi,j where index O corresponds to the bypass function and indices i, j correspond to the plates between which the bypass is carried out.

More generally, a simulated moving bed comprises at least four chromatographic zones, advantageously four or five, whereby each of these zones consists of at least one column or column section. The set of these columns or column sections forms a closed loop, whereby the recycling pump between two sections is regulated in flow rate.

Figure 4A:
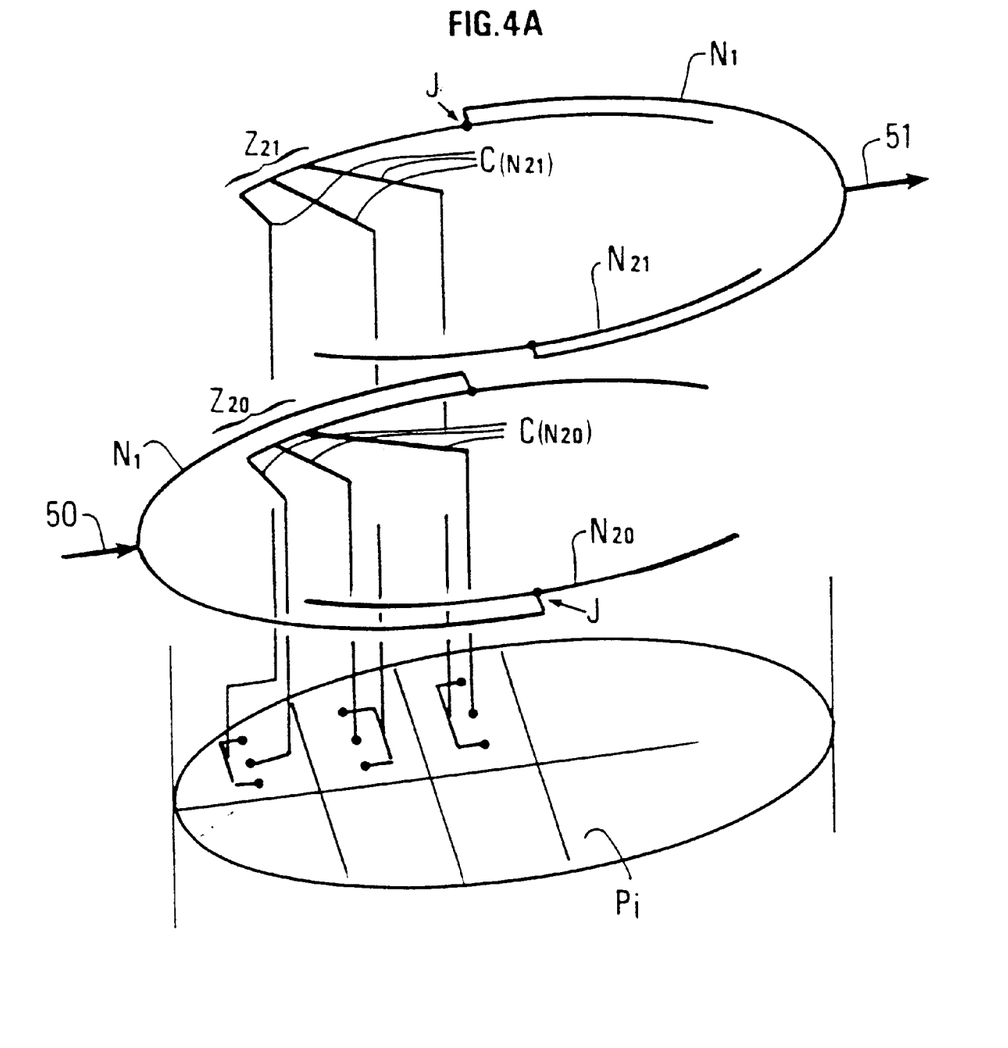
FIGS. 4A, 4B and 4C represent several variant embodiments of a fluid distributing-collecting system.
Figure 4B:
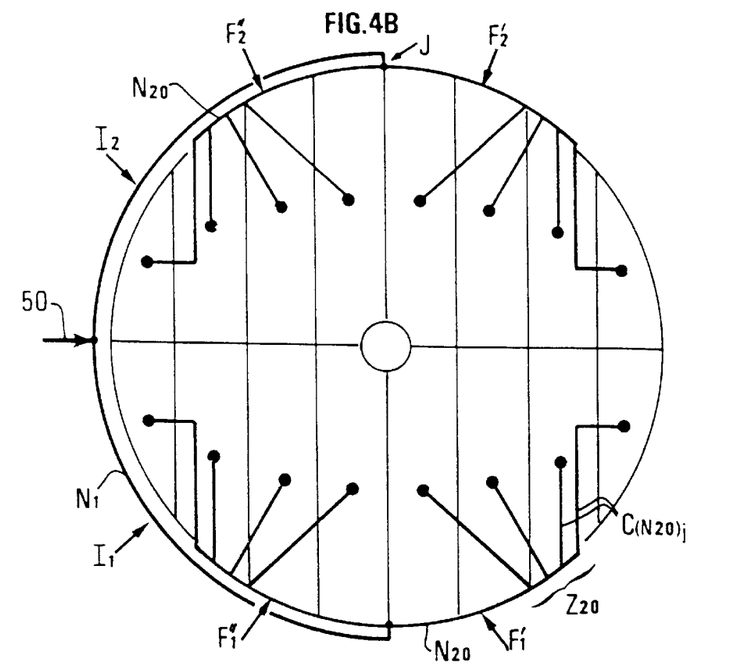
Figure 4C:
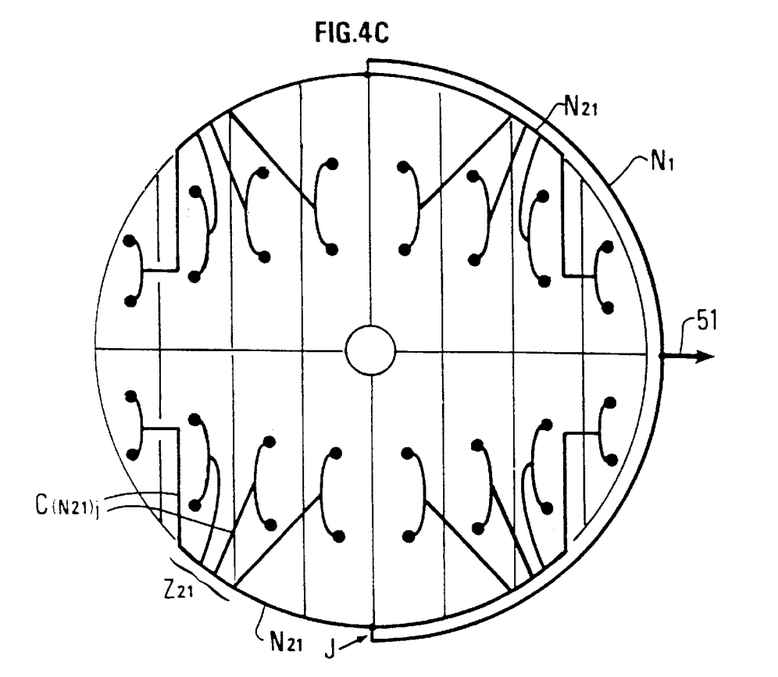

These different lines can be connected with a distributing-collecting system whose function is to minimize the dispersions in the passage times of fluids and that has one of the characteristics that are described in FIGS. 4A to 4C.

Without exceeding the scope of the invention, any network for distribution or extraction of secondary fluids that are commonly used for the separation columns by adsorption can be used.

FIGS. 4A, 4B and 4C show a perspective view and views in section of a secondary circuit that makes it possible to distribute or to extract secondary fluids at the level of different panels for a given plate, for example. The geometry and the hydraulic characteristics of this network are selected to obtain a distribution of secondary fluids that is the most symmetrical possible for the set of panels or distribution rails of a plate. In particular, this distribution is selected to ensure a low imbalance index and to reduce the dispersion time relative to distribution systems according to the prior art.

The example that is given as an illustrative and nonlimiting example relates to a distributing-collecting system that is suited for an essentially cylindrical column.

Plate Pi (FIGS. 4B, 4C) has, for example, the shape of a disk. It is cut into several DME according to a cutaway in parallels (of meridian type), whereby the panels or DME of a plate preferably has essentially identical widths. Such a cutaway ensures a surface density of essentially constant drainage for the panels.

For plates that are cut out into four sectors, the DME number per sector is preferably even.

The number of systems that are associated with a separation column is a function of the geometry of the DME, for example.

In the variant embodiment that is described in FIG. 4A, a distributing-collecting system is linked with one of the two rails of the DME:

a so-called annular level 1 chamber $N_1$ communicates with the outside of the column with a hose 50 or 51, for example. These hoses allow the introduction and/or the extraction of fluids. They can have specific functions, injection or extraction. Annular chamber $N_1$ with a rectangular section, for example, extends in the internal periphery of the adsorbent bed and ensures in particular a two-way division or collection of the circulating flow rate of the fluids, a so-called annular level 2 chamber $N_2$ of rectangular section, for example, is placed on the periphery of the adsorbent. In particular according to its function (injection, extraction or injection/draw-off), it ensures respectively a division or a collection or else a two-way division and/or collection of the fluid flow rate.

Its position according to the function of the distributing-collecting system, because of the geometric space requirement, can be arranged, for example, above (referenced $N_{21}$) or below (referenced $N_{20}$) chamber $N_1$.

Junction J of a chamber $N_{20}$, $N_{21}$ with level 1 chamber $N_1$ is carried out, for example, with half of the periphery of its length.

An annular level 2 chamber comprises, for example, at each of its ends, one or more connecting hoses $C(N_{20})]$ or $C(N_{21})]$ with the panels of a plate, and index j corresponds to the index of a panel that is connected with the hoses. A hose $C(N_{20})_j$ or $C(N_{21})]$ is connected to a zone $Z_{20}$, $Z_{21}$ of the annular chamber that is concerned ($N_{21}$ or $N_{22}$).

The length of a so-called annular level 1 chamber or $N_1$ is, for example, equal to half of the perimeter of the plate.

The length of a so-called annular level 2 chamber or $N_2$ is in an angular sector of 20 to 160 degrees and preferably between 100 and 120 degrees.

Zone $Z_{20}$, $Z_{21}$ can be identified by an angle $\alpha$ counting from a radius of the plate, for example the radius that passes through junction point J and relative to the central point of the zone. Length Zr of the zone is determined by, for example, the angular sector that is defined by $\alpha +/- \epsilon$, bounded by angles $\alpha_{min}$ and $\alpha_{max}$.

The value of angle $\alpha$ will be in, for example, the range (10 degrees, 80 degrees) and preferably in the range (40 degrees, 70 degrees).

The angular sector value will be selected in the interval (3 degrees, 30 degrees) and preferably in the interval (7 degrees, 15 degrees), which corresponds to length Zr of zones $Z_{20}$ and $Z_{21}$.

An effort is made to ensure as star-shaped an arrangement of hoses as possible to obtain the smallest dispersion time in the distribution or extraction of the fluids. The connecting points of the hoses are grouped virtually at the same point of the zone in the smallest possible angular sector.

The positioning of the connecting hoses, and the selection of the angular sector make it possible in particular to reduce the pure delay time and dispersion time. This delay time can thus be reduced to 10 s.

Each hose $C(N_{20})]$, $C(N_{21})]$ for distribution and/or extraction has a diameter dj, a length lj and a connecting point rj with a level 2 chamber that is located in corresponding zone $Z_{20}$, $Z_{21}$.

Different parameters, $\alpha$, $\epsilon$ and li, are selected so that the fluids that are distributed arrive at approximately the same time in all of the panels that form a plate or in the case of the extraction of fluids reach hoses 50, 51 at approximately the same time.

Diameter dj of a hose is determined based on the flow rate of the fluid that circulates to ensure a fluid circulation rate that is approximately identical in the various hoses.

A hose can be linked with one or more DME panels. In this case, it is extended by branches up to a rail for distributing or collecting of the panel.

FIGS. 4B and 4C show a plate that comprises several DME, whereby the plate is divided into four sectors according to a cutaway in parallels (of meridian type). The number of panels in this case will preferably be an even number.

FIG. 4B shows the distributing-collecting system that ensures the injection of a fluid in lower rail 7, whereas FIG. 4C shows the distributing-collecting system that ensures the draw-off from upper rail 6.

For example, by taking into consideration a group of the fluids by function, the feedstock and the solvent are injected into a DME whereas the extract and the raffinate are drawn-off from a DME.

Injection (FIGS. 4A, 4B)

Four hoses $C(N_{20})j$ with j varying from 1 to 4 make possible the injection of fluid to four DME of a quarter plate sector, the feedstock and the desorbent are introduced via hose 50 into annular chamber $N_1$. The injected flow is divided into two flows that travel through paths 11 and 12 and that correspond approximately to one half of the semi-circumference of the plate. Each flow then travels into annular chamber $N_{20}$, in which it is divided into two flows F'1 and F"1. Each flow is then distributed from connecting hoses $C(N_{20})j$ that are grouped in zone $Z_{20i}$ at lower rail 7 of each of the DME.

The flows that are obtained from orifices 7i will strike the end of deflectors 5a, 5b and are mixed with the main fluid space.

Extraction or Draw-off (FIGS. 4A. 4C)

Four hoses $C(N_{21})j$ will make it possible to extract a fluid from 4 panels or DME, the extract and the raffinate are drawn off from a rail of a panel, for example upper rail 6, and two hoses ($20_1$, $20_2$) (FIG. 2A). They then pass through connecting hoses $C(N_{21})j$ that are linked with zone $Z_{21}$ of a chamber $N_{21}$. The two flows of fluids that are collected in the zones that are positioned at the two ends of annular chamber $N_{21}$ are grouped before passing into annular chamber $N_1$ in connection with hose 51 that recovers all of the flows that are obtained from the four sectors of the plate.

The given parameters for a DME and for the distributing-collecting system above by way of example in relation with a separation column of an approximately cylindrical shape can be applied, without exceeding the scope of the invention, to a separation column that has any shape whatsoever, whereby the distributing-collecting system then has a shape that is suited to that of the column.

Likewise, a plate can be divided into several DEM according to a cutaway other than the cutaway in parallels, for example into sectors of pie chart type.

In a general manner, grouping of the secondary fluids can be carried out, for example, in three given ways as an illustrative and nonlimiting example to illustrate the connections of the column with the outside.

Based on the groupings of the fluids, rails 6 and 7 ensure different functions: a distribution function, an extraction function or else the two functions.

Case of Grouping Fluids By Function

It was presented above in connection with FIGS. 4A, 4B and 4C.

Case of Grouping Fluids By Nature

The fluids that are being considered as characteristic fluids are the desorbent and the extract and the so-called "dirty" fluids, the raffinate and the feedstock.

In this case, rails 6 and 7 ensure the two distribution and extraction functions.

Case of Grouping By Flow Rate

The fluids that have, for example, a low flow rate will be the feedstock, and the extract that has a high flow rate will be the desorbent and the raffinate.

In this case, rails 6 and 7 ensure the two distribution and extraction functions.

In these two latter grouping examples, the fluids that are injected via openings 6i and 7i will strike a portion of the solid walls respectively of wall 8 and deflectors 5a, 5b. They pass through the distributing-collecting system in connection with the panel, whereas the fluids that are to be extracted are collected in rails 6 or 7 before being sent via connecting hoses to the annular chambers that are mentioned above.

Without exceeding the scope of the invention, the DME and the distributing-collecting system that are described above can easily be used in separation devices that may or may not comprise a central holding beam and that have a diameter that varies, for example, from 3 to 10 m.

They can also be used for separation columns that have a diameter that is less than or equal to 5 m and that do not comprise a central support beam.

In the preceding description, the terms "rail" and "circuit" are used interchangeably. Other possible synonyms are "channel" and "trough".

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/10.996, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A device (DME) or panel for collecting, distributing, mixing or drawing off several fluids, at least one main fluid and at least two secondary fluids comprising:

means for collecting a main fluid (3, 9), at least two injection and/or draw-off rails (6, 7) that allow the passage of secondary fluids, at least two mixing chambers (11a, 11b) that communicate with injection and/or draw-off rails (6, 7) with orifices or passages (6i, 7i), means (12, 4) for redistributing the fluid that is obtained from said mixing chambers, means (5a, 5b) for separating collecting and redistributing means, characterized in that said rails (6, 7) comprise an upper rail (6) and a lower rail (7) arranged one above the other, and in that said mixing chambers (11a, 11b) are arranged on both sides of at least one of said rails.

2. A device according to claim 1, wherein said mixing chambers (11a, 11b) are arranged relative to orifices (6i, 7i) to obtain an injection or a draw-off of the fluid or fluids that is the most uniform possible in said mixing chamber(s).

3. A device or panel according to claim 1, wherein said rails and said mixing chambers are located approximately in the center of gravity of the surface of said DME.

4. A device according to claim 1, wherein the upper rail (6) is provided with at least two hoses ($20_1$, $20_2$) and wherein the lower rail (7) is provided with at least one hose (21), whereby said hoses are arranged to ensure the circulation of secondary fluids in the most homogeneous way in the rails and mixing chambers (11a, 11b).

5. A device according to claim 1, wherein openings (6i, 7i) for passage of a secondary fluid from rail(s) (6,7) whose function is to inject secondary fluids into a mixing chamber (11a, 11b) has an axis such that the fluid that is obtained strikes at least a portion of a solid wall of one of elements (5a, 5b, 8a, 8b) of the DME.

6. A device according to claim 1, wherein lower rail (7) of the secondary fluid has its lower wall arranged at lower grid (4).

7. A device according to claim 6, wherein openings (6i, 7i) of the rail or rails that have an injection function are arranged such that the fluid jet that passes through strikes at least a portion of a solid wall of one of the elements of the DME.

8. A device that comprises a chamber (30), wherein said chamber comprises at least a first adsorbent bed ($A_1$) and at least a second adsorbent bed ($A_2$), wherein said beds are separated by a plate (Pi) that comprises one or more panels (DME) according to claim 1, wherein said DME are linked with the outside via several connecting hoses (20, 21, $C(N_{21})$, $C(N_{20})$).

9. A device according to claim 8, wherein said upper rail (6) of a DME has a function of collecting fluids, and said lower rail (7) of a DME has a fluid injection function.

10. A device according to claim 8, wherein said upper rail (6) of a DME has a function of injecting fluids, and said lower rail (7) of a DME has a function of collecting fluids.

11. A device according to claim 8, wherein said upper rail (6) and lower rail (7) of a DME each have a fluid injecting-collecting function.

12. A device according to claims 8, wherein openings (6i, 7i) are arranged alternately or at random.

13. A device according to one of claim 8, wherein the parameters of rails (6, 7) and openings (6i, 7i) are selected from among the following data:

a diameter of the openings of between 2 and 15 mm, a perforation span of between 25 and 400 mm, a rate of flow of the fluids of 3–20 m/s, and the value of the span that is being considered with the value of the rate makes it possible to obtain a good mixing of the secondary fluid and the main fluid.

14. A device according to claim 13, wherein the diameter of the openings is between 4 and 7 mm; the perforation span is between 50 and 200 mm; and the rate of flow of fluids is 5–15 m/s.

15. A device according to claim 8, wherein the parameters of the mixing chambers and the openings of said chambers are selected from among the following values:

a diameter of openings (8ai, 8bi) of between 5 and 50 mm, a perforation span that is selected from the interval of 25–400 mm, a rate of flow of the mixture of between 0.5 and 3.5.

16. A device according to claim 15, wherein the diameter of openings is between 10 and 25 mm; the perforation span is 50–200 mm; and the rate of flow of the mixture is 1.0–2.0 m/s.

17. A device according to claim 8, comprising at least two systems for distributing fluids that have the following characteristics:

said distribution system is placed on the periphery of said chamber (30), said distribution system is connected with at least one distribution plate (Pi), said distribution system comprises:

at least one hose (50, 51) that makes it possible for the device and the outside to communicate, at least one so-called level 1 chamber ($N_1$) in connection with hose (50, 51) that ensures a two-way division or collection of the fluid flow, at least two so-called level 2 chambers ($N_{20}$, $N_{21}$), whereby the level 2 chambers ensure a two-way division or collection of the flow of the fluid that comes from or is sent to level 1 chamber ($N_1$), one or more connecting hoses ($C(N_{20})_j$, $C(N_{21})j$)) that extend between a level 2 chamber ($N_{20}$, $N_{21}$) and at least one of panels (DME) of a plate (Pi), whereby points rj for connecting said connecting hoses are located in a zone ($Z_{20}$, $Z_{21}$), whereby the positioning of this zone is determined by an angle α counting from one of the radial axes of said plate (Pi), whereby each of the fluid connecting hoses has a length li, whereby the value of each of lengths li, of angle α and of length Zr of the zone are selected so that the passage time of the fluids between a panel (DME) of a plate (Pi) and hose or hoses (50, 51) for introducing or extracting the fluids is approximately identical for all of the fluids.

18. A device according to claim 17, wherein a plate Pi is divided into four sectors.

19. A device according to claim 17, wherein each plate (Pi) is divided into several panels or DME according to a cutaway in parallels.

20. A device according to claim 17, wherein angle α is between 30 and 90 degrees, and wherein length Zr that corresponds to angle sector α+/−ε is between 3 and 30 degrees.

21. A device according to claim 20, wherein angle α is between 50 and 60°, and Zr is between 7 and 15°.

22. A device according to claim 8 in the form of a separation column.

* * * * *

UNITED STATES PATENT AND TRADEMARK OFFICE
CERTIFICATE OF CORRECTION

PATENT NO.        : 6,224,762 B1                                           Page 1 of 1
APPLICATION NO.   : 09/389073
DATED             : May 1, 2001
INVENTOR(S)       : Gilles Ferschneider et al.

It is certified that error appears in the above-identified patent and that said Letters Patent is hereby corrected as shown below:

Column 14, line 8, reads "0.5 and 3.5." should read -- 0.5 and 3.5 m/s. --

Signed and Sealed this

Twenty-seventh Day of February, 2007

JON W. DUDAS
*Director of the United States Patent and Trademark Office*